United States Patent [19]
Trost et al.

[11] Patent Number: 6,130,337
[45] Date of Patent: Oct. 10, 2000

[54] ENANTIOMERICALLY ENRICHED α,α-DISTRIBUTED AMINO ACIDS AND METHOD

[75] Inventors: Barry M. Trost, Los Altos Hills; Javier Ariza Piquer, Union City, both of Calif.

[73] Assignee: Board of Trustees of Leland Stanford Junior University, Stanford, Calif.

[21] Appl. No.: 08/832,713

[22] Filed: Apr. 11, 1997

[51] Int. Cl.[7] .................. C07D 263/04; C07D 263/18; C07D 263/42
[52] U.S. Cl. .................. 548/225; 548/228; 548/229
[58] Field of Search .................. 548/225, 228, 548/229

[56] References Cited

U.S. PATENT DOCUMENTS

| | | | |
|---|---|---|---|
| 3,440,278 | 4/1969 | Kallischnigg | 260/519 |
| 4,264,771 | 4/1981 | Steglich | 548/228 |
| 4,339,589 | 7/1982 | Steglich | 548/228 |
| 4,508,921 | 4/1985 | Amato | 562/443 |
| 4,981,972 | 1/1991 | Kobori | 548/228 |
| 5,039,813 | 8/1991 | Fazio | 548/228 |
| 5,691,278 | 11/1997 | Park | 504/252 |

FOREIGN PATENT DOCUMENTS

| | | |
|---|---|---|
| 0344963 | 12/1989 | European Pat. Off. . |
| 19533617 | 3/1997 | Germany . |
| 1469307 | 4/1977 | United Kingdom . |
| 95/12573 | 5/1995 | WIPO . |
| 96/09306 | 3/1996 | WIPO . |

OTHER PUBLICATIONS

Bartlett et al., "Ester–Enolate Claisen Rearrangement of Alpha–Amino Acid Derivatives", Journal of Organic Chemistry, vol. 47, No. 20, Sep. 24, 1982, pp. 3933–3941.

Trost et al., "Catalytic Asymmetric Alkylation of Nucleophiles: Asymmetric Synthesis of Alpha–Alkylated Amino Acids", Angewandte Chemie. International Edition, vol. 36, No. 23, Dec. 15, 1997, pp. 2635–2637.

Chemical Abstracts 98:53740, abstract of Heterocyclis, (1982), vol. 19(10), pp. 1823–1828, Tsuge.

Chemical Abstracts 90:23638, 1978.

CA 113:168298, 1990.
CA 100:121298, 1983.
CA 126:59963, 1996.
CA 113:152213, 1990.
CA 106:85002, 1986.
CA 103:22934, 1985.
CA 102:96084, 1984.
CA 101:151379, 1984.
CA 101:131107, 1984.
CA 101:73096, 1984.
CA 95:187613, 1981.
CA 91:21019, 1979.
CA 90:39214, 1978.
CA 70:106832, 1969.
CA 125:104859, 1996.
CA 123:144634, 1994.
CA 122:4968, 1993.
CA 117:146711, 1992.
CA 73:131303, 1970.

Almond et al., "Interaction of α–Chrmotrypsin with Several α–Methyl–α–Acylamino Acid Methyl Esters," *Biochemistry*, 1:2 (Mar. 1962), pp. 243–249.

Pankaskie et al., "Inhibitors of Polyamine Biosynthesis. 8. Irreversible Inhibition of Mammalian S–Adenosyl–L–methionine Decarboxylase by Substrate Analogues," *J. Med. Chem.*, 23 (1980), pp. 121–127.

Burgess, Antony W., "Designing Amino Acids to Determine the Local Conformations of Peptides," *Proc. Natl. Acad. Sci. USA*, 91, (Mar. 1994), pp. 2649–2653.

Koert, Ulrich, "Oligo–(thiazolin)–Naturstoffsynthese," *Nachr. Chem. Tech. Lab.*, 43 (1995), pp. 347–354.

*Primary Examiner*—D. Margaret Seaman
*Attorney, Agent, or Firm*—Majestic, Parsons, Siebert & Hsue P.C.

[57] ABSTRACT

Compositions and methods for the preparation of enantiomerically enriched α,α-disubstituted amino acid precursors are presented. Briefly, allylic electrophiles are alkylated with oxazolones in the presence of a base and catalytic quantities of a transition metal complex incorporating a chiral phosphine ligand to yield 4,4-disubstituted-5(4H)-oxazolones. These precursors may be subsequently transformed either synthetically or enzymatically to yield enantiomerically enriched α,α-disubstituted amino acids.

17 Claims, No Drawings

ENANTIOMERICALLY ENRICHED α,α-DISTRIBUTED AMINO ACIDS AND METHOD

FIELD OF THE INVENTION

The present invention relates to the preparation of enantiomerically enriched 4,4-disubstituted-5(4H)-oxazolones, which can be transformed into enantiomerically enriched α,α-disubstituted amino acids.

BACKGROUND OF THE INVENTION

α,α-Disubstituted amino acids are of great interest for a variety of reasons. They have been shown to be effective inhibitors of enzymes which normally metabolize the corresponding proteinogenic amino acids (Almond et al., *Biochem.*, 1, 243 (1962); Pankaskie et al., *J. Med. Chem.*, 23, 121 (1980)). The additional substituent of such amino acids can have a marked effect on the conformation of peptide structure, thus they can be utilized to modify physiologically important peptides to stabilize preferred conformations (Burgess, *Proc. Natl. Acad. Sci. USA*, 91, 2649 (1994)). They also occur as constituent parts of interesting natural products (Koert, *Nachr. Chem. Tech. Lab.*, 43, 347 (1995)). As such any effective preparation of α,α-disubstituted amino acids, in an enantiocontrolled fashion, is highly desirable.

5(4H)-Oxazolones have been known for some time, and are prepared by the direct dehydration of N-acylated α-amino acids. These 5(4H)-oxazolones are readily substituted in the 4-position. Subsequent hydrolysis of 4,4-disubstituted-5(4H)-oxazolone ring results in α,α-disubstituted amino acids. However, it has not been previously known to substitute the ring system in an stereospecific fashion so as to generate enantiomerically enriched, α,α-disubstituted amino acids.

SUMMARY OF THE INVENTION

The present invention relates compositions and methods for the preparation of enantiomerically enriched α,α-disubstituted amino acid precursors.

In one aspect of the present invention, methods for preparing enantiomerically enriched α,α-disubstituted amino acids precursors are presented. Briefly, allylic electrophiles are alkylated with oxazolones in the presence of a base and catalytic quantities of a transition metal complex incorporating a chiral phosphine ligand. In addition to the surprising degree of enantioselectivity, a high degree of diastereoselectivity may also be achieved with the appropriate choice of substrate, base and solvent.

A particularly preferred chiral phosphine ligand for practicing the present invention is Compound 1.

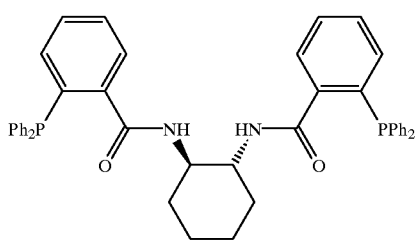

(1)

Preferred oxazolones for the practice of the present invention are compounds of Formula 3

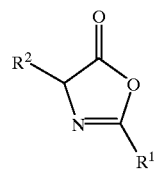

(3)

wherein $R^1$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls and $R^2$ is an amino acid side-chain, a substituted amino acid side-chain or is selected from a group consisting of substituted and unsubstituted $C_1$–$C_{20}$ alkyls, substituted and unsubstituted $C_1$–$C_{20}$ aryls, and substituted and unsubstituted $C_1$–$C_{20}$ heteroaryls. Particularly preferred oxazolones are where $R^1$ is phenyl and $R^2$ is an amino acid side-chain.

Preferred allylic electrophiles ($R^3$-L) are compounds of Formula 4 and Formula 6.

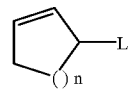

(4)

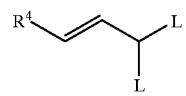

(6)

When the allylic electrophile is cyclic, then n=1–6 and L is any ionizable group (also referred to as a leaving group). Illustrative examples of leaving groups include but are not limited to halides, esters, carbonates, and carboxylates. A particularly preferred cyclic allylic electrophile is where n=1 and L is acetate.

When the allylic electrophile is acyclic, two leavings groups L are present, and after reaction with an oxazolone of Formula 3, one of the leaving groups L is retained in the product. Similarly to cyclic allylic electrophiles, illustrative examples of leaving groups include but are not limited to halides, esters, carbonates, and carboxylates. The substituent $R^4$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls. A particularly preferred acyclic allylic electrophile is where L is acetate are acetate and $R^4$ is either hydrogen or a phenyl.

DESCRIPTION OF THE PREFERRED EMBODIMENTS

This invention is based on the discovery that allylic electrophiles may be alkylated with 5(4H)-oxazolones with high enantioselectivity, in the presence of a base and catalytic quantities of a transition metal complex incorporating a chiral phosphine ligand. This reaction results in enantiomerically enriched 4,4-disubstituted-5(4H)-oxazolones which may be subsequently transformed to yield enantiomerically enriched α,α-disubstituted amino acids.

As used in this disclosure, "enantiomerically enriched" refers to products whose enantiomeric excess is greater than zero. Enantiomeric excess (ee) is the "excess" of one enantiomer over the other. As a result, since both enantiomers are present in equal amounts in a racemic mixture, the enantiomeric excess would be zero (0% ee). However, if one enantiomer is enriched such that it constitutes 95% of the product, then the enantiomeric excess would be 90% ee (95% −5% (the amount of the enriched enantiomer minus the amount of the other enantiomer)). In general, higher enantiomeric purity (>about 50% ee) is preferred with enantiomeric excess of between about 75% ee and about 90% ee being more preferred and enantiomeric excess of greater than about 90% ee being particularly preferred.

Suitable transition metal complexes for practicing the invention are those based on Pd, W, Mo, Rh, Ni, and mixtures thereof (e.g. Pd and Rh). Especially preferred in the practice of the present invention are complexes of Pd(0) with C2-symmetric bidentate diphosphines containing a pair of metal binding moieties of the type C(=O)—Ar—P—(Ar')$_2$, wherein Ar and Ar' are aryl or heteroaryl groups, optionally comprising fused rings, as disclosed by Trost and Bunt in Wo-A-9609306, published Mar. 8, 1996. A particularly preferred ligand is compound (1). Such C2-symmetric ligands are available in both enantiomeric forms, thereby allowing with equal facility the preparation of a chosen enantiomer of a target compound.

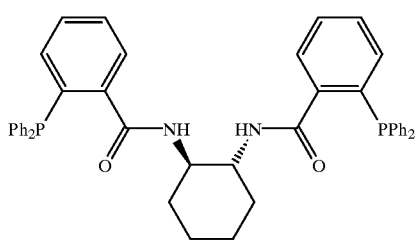

(1)

5(4H)-Oxazolones are well known in the literature. As illustrated by Scheme 1, one general method for their preparation is the direct dehydration of the corresponding N-acylated α-amino acid (2). Briefly, N-acyl α amino acids (2) are treated with N,N'-dicyclohexylcarbodiimide (DCC) in THF for 24 hours. The only by-product, N,N'-dicyclohexyl urea (DCU), may be removed by simple filtration at low temperature which results in high yields of pure 5(4H)-oxazolones (3). However, although Scheme 1 has been described, oxazolones may be prepared using any synthesis known in the art.

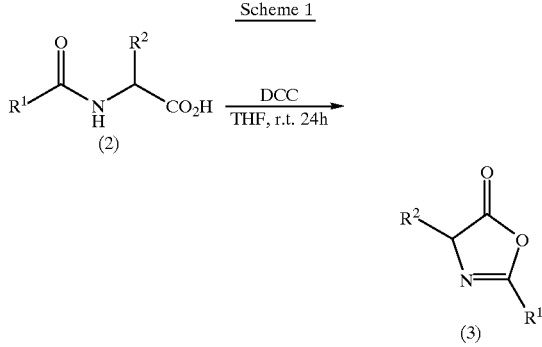

Scheme 1

Preferred oxazolones for the practice of the present invention are compounds of Formula 3 (as illustrated by Scheme 1) wherein $R^1$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls and $R^2$ is an amino acid side-chain, a substituted amino acid side-chain or is selected from a group consisting of substituted and unsubstituted $C_1$–$C_{20}$ alkyls, substituted and unsubstituted $C_1$–$C_{20}$ aryls, and substituted and unsubstituted $C_1$–$C_{20}$ heteroaryls. Particularly preferred oxazolones are where $R^1$ is phenyl and $R^2$ is an amino acid side-chain.

In one embodiment of the present invention, cyclic allylic electrophiles are used. As shown by Scheme 2, cyclic allylic electrophiles are alkylated with 5(4H)-oxazolones in the presence of a base and a catalytic amount of a Pd(0)-diphosphine complex to give novel products of the formula (5). The enantiomeric purity of the 4, 4-disubstituted-5(4H)-oxazolones (5) is typically high and often exceed 95% ee. The diastereomeric ratio is largely dependent upon the substrate, solvent and base and ranges between 1:1 to only a single diastereomer being observed.

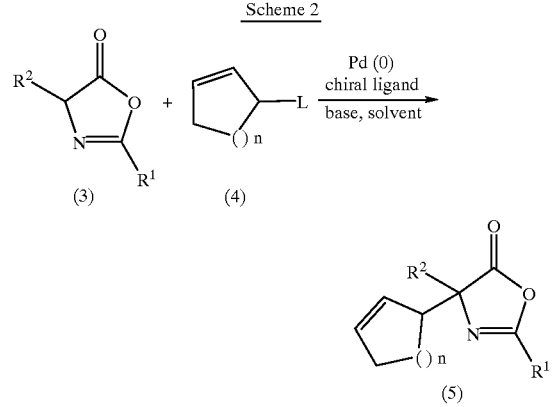

When the allylic electrophile is cyclic, then n=1–6 and L is any ionizable group (also referred to as a leaving group). Illustrative examples of leaving groups include but are not limited to halides, esters, carbonates, and carboxylates. A particularly preferred cyclic allylic electrophile is where n=1 and L is acetate. The 5(4H)-oxazolones are as previously defined.

In addition to the surprising degree of enantioselectivity in the synthetic methods of the present invention, a high degree of diastereoselectivity may also be achieved with the appropriate choice of substrate, base, and solvent. Suitable solvent and base combinations include: THF and DME with NaH; $CH_2Cl_2$, $CH_3CN$, DMF, DMSO with $Et_3N$ (and other tertiary amines), or $Cs_2CO_3$. For example, in the case when the catalyst is a Pd(0) complex of the ligand (1), $R^1$=phenyl, $R^2$=methyl, n=2, and L=acetate with $CH_2Cl_2$ (solvent) and $Et_3N$ (base), the product (5) is obtained in a diastereomeric ratio of 2.75:1, with each diastereomer having 99% ee. In contrast, when $R^1$=phenyl, $R^2$=CH($CH_3$)$_2$, n=2, and L=acetate with $CH_3CN$ and $Et_3N$, only a single diastereomer is observed having 99% ee.

In another embodiment of the invention, the reaction is as in Scheme 2 except that acyclic allylic electrophiles are used. As shown by Scheme 3, each L group is a leaving group. Suitable examples of leaving groups include but are not limited to halides, esters, carbonates, and carboxylates. The substituent $R^4$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls. A particularly preferred acyclic allylic electrophile is where L=acetate and $R^4$ is either hydrogen or phenyl.

Scheme 3

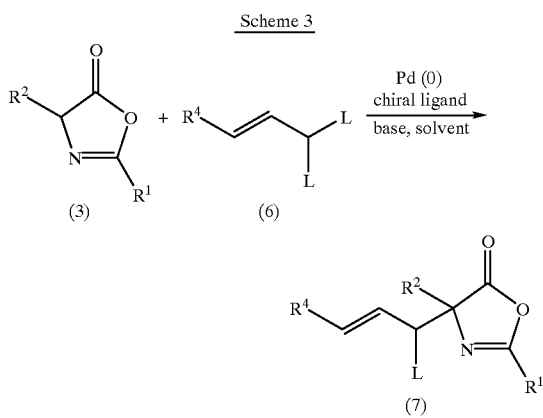

The product of this reaction (7) is also novel. Typically, the enantiomeric purity of the 4,4-disubstituted-5(4H)-oxazolones (7) is high and often exceeds 95% ee. The diastereomeric ratio is largely dependant upon the substrate, solvent and base, and ranges between 1:1 and to only a single diastereomer being observed. For example, when the catalyst is a Pd(0) complex of the ligand (1), $R^1$ and $R^4$=phenyl, $R^2$=methyl, and L=acetate with $CH_2Cl_2$ (solvent) and $Et_3N$ (base), then the product (7) is obtained in a diastereomeric ratio of 4.4:1, each diastereomer having 83% ee and 40% ee, respectively. In contrast, when the catalyst is Pd(0) complex of ligand (1), $R^1$ and $R^4$=phenyl, $R^2$=$CH(CH_3)_2$, and L=acetate with DME and NaH, only a single diastereomer is observed having 99% ee.

The enantiomerically enriched 4,4-disubstituted 5(4H)-oxazolones may be readily transformed into enantiomerically enriched α,α-disubstituted amino acids of Formula 8 (where $R^3$ and $R^2$ are as previously defined) using well known reactions (including enzymatic reactions) known in the art. For example, hydrolysis of the heterocyclic ring affords an N-acyl α-amino acid. Similarly, alcoholysis of the heterocyclic ring affords an N-acyl α-amino ester.

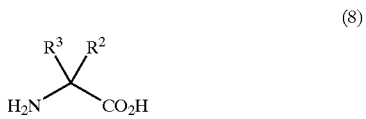

(8)

Aspects of the present invention will now be illustrated by the following examples. It will be understood that these examples are intended to illustrate, and not limit, the present invention.

EXAMPLE 1

All reactions were carried out under Ar atmosphere using standard syringe, septum equipment, and dried solvents which were bubbled with Ar prior use unless otherwise noted. THF, diethyl ether, dimethoxyethane, and dioxane were distilled over sodium benzophenone ketyl; benzene $CH_2Cl_2$ distilled from $CaH_2$; acetonitrile, DMSO and DMF were dried over molecular sieves. 2-Cyclopentenol, 2-cyclopentenyl acetate, 2-cyclohexenyl acetate, and bis($\eta^3$-allyl)di-μ-chloro- dipalladium(II) were prepared by literature methods. Melting points were taken on a Thomas-Hoover melting point apparatus in open capillaries and are uncorrected. $^1H$ NMR (300 MHz) and $^{13}C$ NMR (75 MHz) were obtained on a Varian Gemini 300 spectrometer. NMR spectra were recorded in $CDCl_3$, and chemical shifts were reported in parts per million relative to tetramethylsilane or $CDCl_3$ (77.0 ppm, $^{13}C$). Infrared spectra were recorded on a Perkin Elmer Paragon 500. Optical rotations were measured at 23–25° C. in $CH_2Cl_2$ on a JASCO DIP-360. Enantiomeric excess were determined by chiral HPLC (Chiracel® OD or Chiralpak® AD column, detection at 254 nm and flow rate 1 mL/min). Flash chromatography was performed on silica gel (Merck Kiegel 60, 230–400 mesh).

EXAMPLE 2

2-Oxazolin-5-ones. General Procedure.

A solution of 1,3-dicyclohexylcarbodiimide (DCC, 5.21 g, 25.0 mmol) in THF (25 mL) was added dropwise to a suspension of N-acyl-amino acid (25.0 mmol) in THF (25 mL) at 0° C. under Ar. After stirring overnight at room temperature, the suspension was filtered at −40° C. under Ar and the precipitate was washed twice with THF (2×20 mL) also at −40° C. The combined organic layer was evaporated to dryness and the obtained 2-oxazolin-5-one was not further purified.

4-Methyl-2-phenyl-2-oxazolin-5-one: m.p.: 37–39° C. (lit. 37–38° C.). IR (neat film from $CDCl_3$): 3064, 2986, 2939, 1822, 1731, 1652, 1580, 1527, 1496, 1451, 1323, 1308, 1258, 1156, 1111, 1048, 999, 912, 879, 809, 780, 696 cm$^{-1}$. $^1H$ NMR (300 MHz, $CDCl_3$) δ: 8.01–7.98 (m, 2H), 7.59 (m, 1H), 7.52–7.46 (m, 2H), 4.46 (q, J=7.6 Hz, 1H), 1.60 (d, J=7.6 Hz, 3H). $^{13}C$ NMR (75.5 MHz, $CDCl_3$) δ: 179.0, 161.8, 132.9, 128.9, 127.9, 60.9, 16.7.

2(2'-Methoxyphenyl)-4-methyl-2-oxazolin-5-one: Oil. $^1H$ NMR (300 MHz, $CDCl_3$) δ: 7.83 (m, 1H), 7.52 (m, 1H), 7.07–7.02 (m, 2H), 3.96 (s, 3H), 4.48 (q, J=7.6 Hz, 1H), 1.61 (d, J=7.6 Hz, 3H).

2-Tert-Butyl-4-methyl-2-oxazolin-5-one: Oil. $^1H$ NMR (300 MHz, $CDCl_3$) δ: 4.21 (q, J=7.5 Hz, 1H), 1.47 (d, J=7.5 Hz, 3H), 1.29 (s, 9H).

4-Benzyl-2-phenyl-2-oxazolin-5-one: m.p.: 68–70° C. (lit. 68–70° C.). $^1H$ NMR (300 MHz, $CDCl_3$) δ: 7.93–7.90 (m, 2H), 7.54 (m, 1H), 7.47–7.42 (m, 2H), 7.27–7.22 (m, 5H), 4.69 (dd, J=6.7, 5.0 Hz, 1H), 3.37 (dd, J=14.0, 5.0 Hz, 1H), 3.18 (dd, J=6.7, 14.0 Hz, 1H).

4-Isopropyl-2-phenyl-2-oxazolin-5-one: m.p.: 48–50° C. (lit. 48–51° C.). IR (neat film from $CDCl_3$): 2967, 2934, 2877, 1822, 1654, 1581, 1495, 1452, 1325, 1297, 1246, 1148, 1131, 1044, 1021, 885, 780, 701 cm$^{-1}$. $^1H$ NMR (300 MHz, $CDCl_3$) δ: 8.02–8.00 (m, 2H), 7.57 (m, 1H), 7.51–7.46 (m, 2H), 4.29 (d, J=4.6 Hz, 1H), 2.38 (m 1H), 1.15 (d, J=6.9 Hz, 3H), 1.02 (d, J=6.9 Hz, 3H). $^{13}C$ NMR (75.5 MHz, $CDCl_3$) δ: 177.9, 161.8, 132.7, 128.8, 127.9, 126.0, 70.6, 31.1, 18.6, 17.4.

4-Isobutyl-2-phenyl-2-oxazolin-5-one: m.p.: 53–55° C. (lit. 45–56° C.). IR (KBr) : 2961, 2930, 2876, 1820, 1655, 1580, 1492, 1473, 1452, 1321, 1302, 1279, 1239, 1155, 1077, 1043, 1020, 897, 882, 851, 818, 782, 697, 659 cm$^{-1}$. $^1H$ NMR (300 MHz, $CDCl_3$) δ: 8.01–7.99 (m 2H), 7.57 (m, 1H), 7.51–7.46 (m, 2H), 4.42 (dd, J=9.1, 5.5 Hz, 1H), 2.06 (m, 1h), 1.85 (m, 1H), 1.68 (m, 1H), 1.04 (d, J=6.9 Hz, 3H), 1.01 (d, J=7.0 Hz, 3H). $^{13}C$ NMR (75.5 MHz, $CDCl_3$) δ: 179.1, 161.5, 132.6, 128.8, 127.9, 126.1, 63.9, 40.7, 25.1, 22.6. 21.8.

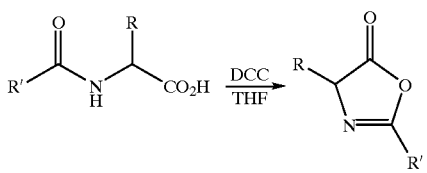

| R | R' | N-acyl-AA | Yield (g) |
|---|---|---|---|
| Methyl | Phenyl | 4.83 g | 99% (4.34 g) |
| Methyl[a,d] | 2-Methoxyphenyl[e] | 2.72 g | 100% (2.53 g) |
| Methyl[b,d] | tert-Butyl[f] | 2.45 g | 90% (1.96 g) |
| Methyl[c,d] | 2-Pyridyl[g] | 0.479 g | — |
| Benzyl | Phenyl | 6.73 g | 89% (5.61 g) |
| Isobutyl[a] | Phenyl | 2.94 g | 83% (2.26 g) |
| Isopropyl[a] | Phenyl | 2.61 g | 83% (2.11 g) |

[a]Scaled to 1/2;
[b]Scaled to 3/5;
[c]Scaled to 1/10;
[d]Prepared from DL-alanine methyl ester hydrochloride;
[e]Prepared from the corresponding acid and DCC-Et$_3$N;
[f]Prepared from pivaloyl chloride and Et$_3$N;
[g]Prepared from the corresponding acid and DCC-Et$_3$N.

EXAMPLE 3
Asymmetric Alkylation of 2-Cyclohexenyl Acetate with 4-Methyl-2-phenyl-oxazolin-5-one. General Procedure.

2-Cyclohexenyl acetate (14 mg, 100 μmol was added to a solution (0.5 mL) of amine (200 μmol) and 4-methyl-2-phenyl-2 oxazolin-5-one (39.4 mg, 225 μmol). Then a preformed solution (0.5 mL) of bis($\eta^3$-allyl)di-$\mu$-chlorodipalladium (II) (0.9 mg, 2.5 μmol) and chiral ligand (7.5 μmol) was added via cannula. The reaction mixture was quenched with aqueous phosphate buffer (pH 7, 20 ml) and extracted with CH$_2$Cl$_2$ (3×15 mL). The combined organic layer were dried over Na$_2$SO$_4$ and concentrated in vacuo. The residue was purified by flash chromatography on silica gel eluting with petroleum ether-AcOEt (95:5) or hexane-AcOEt (95:5) to give an oil as a non-separable diastereomeric mixture of 4(2'-cyclohexenyl)-4-methyl-2-phenyl-2-oxazolin-5-one. Then, enantiomeric and diastereomeric excess were determined by chiral HPLC (Chiracel® OD column, heptane/2-propanol 99.9:0.1), $t_R$(major)=8.5 (1'R, 4R), 14.0 (1'S, 4S), $t_R$(minor)=10.5 (1'S, 4R), 16.3 (1'R, 4S). Further separation could be accomplished by careful flash chromatography on silica gel eluting with petroleum ether-AcOEt (97:3).

(1'S, 4S)-4(2'-Cyclohexenyl)-4-methyl-2-phenyl-2-oxazolin-5-one: Oil. [α]$_D$ −82.4 (c=1.03, CH$_2$Cl$_2$). IR (neat film from CDCl$_3$): 3031, 2936, 2862, 1820, 1655, 1581, 1494, 1451, 1320, 1291, 1003, 920, 873, 779, 704, 692, 668 cm$^{-1}$. $^1$H NMR (300 MHz, CDCl$_3$) δ: 8.01–7.98 (m, 2H), 7.56 (m, 1H), 7.50–7.45 (m, 2H), 5.84 (m, 1H), 5.53 (m, 1H), 2.64 (m, 1H), 1.98–1.93 (m, 3H), 1.85 (m, 1H), 1.59–1.49 (m, 2H), 1.54 (s, 3H). $^{13}$C NMR (75.5 MHz, CDCl$_3$) δ: 180.7, 159.6, 132.6, 131.4, 128.8, 128.0, 126.1, 124.8, 71.9, 43.1, 24.7, 23.5, 21.4, 20.9. Anal. Calcd for C$_{16}$H$_{17}$NO$_2$; C, 75.27; H, 6.71; N, 5.49. Found: C, 75.46; H, 6.75; N, 5.58.

(1'S, 4R)-4(2'-Cyclohexenyl)-4-methyl-2-phenyl-2-oxazolin-5-one: Oil. [α]$_D$ −96.2 (c=1.25, CH$_2$Cl$_2$). IR (neat film from CDCl$_3$): 3029, 2935, 2861, 1818, 1654, 1581, 1494, 1451, 1321, 1291, 1002, 922, 876, 702, 692 cm$^{-1}$. $^1$H NMR (300 MHZ, CDCl$_3$) δ: 8.03–8.00 (m, 2H), 7.58 (m, 1H), 7.51–7.46 (m, 2H), 5.88 (m, 1H), 5.65 (m, 1H), 2.64 (m, 1H), 1.98–1.96 (m, 2H), 1.84–1.78 (m, 2H), 1.58–1.49 (m, 2H), 1.56 (s, 3H). $^{13}$C NMR (75.5 MHZ, CDCl$_3$) δ: 180.4, 160.1, 132.7, 131.5, 128.8, 128.0, 126.0, 124.1, 71.8, 42.4, 24.8, 23.3, 21.6, 21.2. Anal. Calcd for C$_{16}$H$_{17}$NO$_2$; C, 75.27; H, 6.71; N, 5.49. Found: C, 75.33; H, 6.74; N, 5.43.

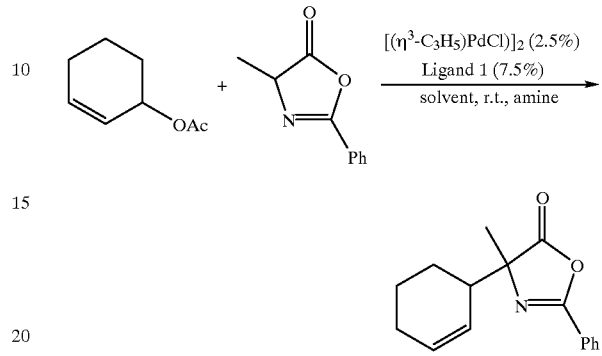

| Solvent | Amine | Time | Amount | Yield | D.r.(e.e) |
|---|---|---|---|---|---|
| CH$_2$Cl$_2$ | Et$_3$N | 18 h | 29 μL | 94% (24.1 mg) | 2.75:1 (99)(99) |
| CH$_2$Cl$_2$ | Hydroquinidine 9-phenanthryl ether | 4 h | 100 mg | 87% (22.2 mg) | 2.83:1 (99)(99) |
| CH$_2$Cl$_2$ | (DHQD)$_2$PHAL | 4 h | 78 mg | 76% (19.3 mg) | 2.84:1 (99)(99) |
| CH$_2$Cl$_2$ | (DHQ)$_2$PYR | 4 h | 88 mg | 94% (23.9 mg) | 2.97:1 (99)(99) |
| CH$_2$Cl$_2$ | (−)-N-Methyl-ephedrine | 7 h | 36.6 mg | 72% (18.4 mg) | 2.92:1 (99)(99) |
| CH$_2$Cl$_2$ | Chirald® | 7 h | 56.7 mg | 82% (20.9 mg) | 2.97:1 (99)(99) |
| CH$_2$Cl$_2$ | 4-DMAP | 9 h | 24.4 mg | 55% (13.8 mg) | 2.92:1 (99)(99) |
| CH$_2$Cl$_2$ | 2,2,6,6-Tetramethyl piperidine | 5 h | 36.2 mg | 57% (14.5 mg) | 2.96:1 (99)(99) |
| CH$_2$Cl$_2$ | (−)-Quinine | 9 h | 64.9 mg | 50% (12.8 mg) | 2.96:1 (98)(98) |
| CH$_2$Cl$_2$ | (−)-Sparteine | 9 h | 46.9 mg | 66% (16.9 mg) | 2.89:1 (99)(98) |
| CH$_2$Cl$_2$ | Quinidine | 9 h | 64.9 mg | 60% (15.4 mg) | 2.92:1 (99)(99) |
| CH$_2$Cl$_2$ | (−)-Nicotine | 18 h | 32.5 mg | 48% (12.2 mg) | 2.99:1 (99)(99) |
| CH$_2$Cl$_2$ | Triethanolamine | 3 h | 27μ | 88% (22.4 mg) | 2.78:1 (99)(99) |
| CH$_2$Cl$_2$ | DBU | 6 h | 61μ | 30% (15.3 mg) | 2.69:1 (99)(99) |
| Toluene | Et$_3$N | 18 h | 29μ | 45% (11.6 mg) | 2.75:1 (99)(99) |
| Toluene | (−)-Nicotine | 24 h | 32μ | 53% (13.4 mg) | 2.83:1 (99)(99) |

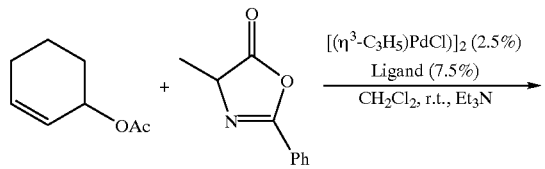

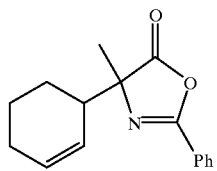

| Ligand | Yield | Time | D.r. (e.e.) |
|---|---|---|---|
| 2[a] (11.0 mg) | 85% (43.2 mg) | 2 h | 1.25:1 (78) (68) |
| 3[a] (15.0 mg) | 95% (48.7 mg) | 2 h 30' | 2.55:1 (62) (62) |
| 4 (5.9 mg) | 76% (19.3 mg) | 14 h | 2.55:1 (90) (92) |

[a]Reaction scaled × 2.

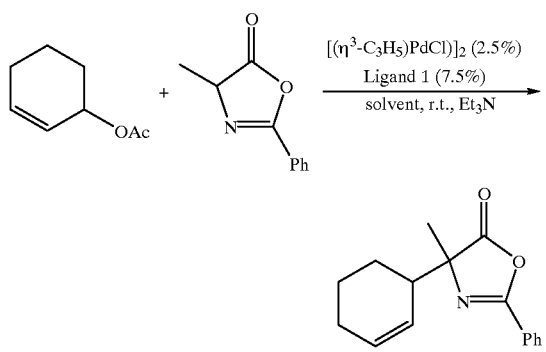

| Solvent[a] | Yield | D.r. (e.e.) |
|---|---|---|
| CH$_3$CN | 90% (45.8 mg) | 8.67:1 (99) (97) |
| DMF | 94% (48.0 mg) | 4.43:1 (98) (96) |
| DMSO | 41% (20.9 mg) | 4.24:1 (98) (95) |

[a]Reaction scaled × 2.

EXAMPLE 4

Asymmetric Alkylation of 2-Cyclohexenyl Acetate with 4-Alkyl-2-phenyl-2-oxazolin-5-one. General Procedure.

2-Cyclohexenyl acetate (28 mg, 200 μmol) was added to a solution of triethylamine (56 μL, 400 μmol) and 4-alkyl-2-phenyl-2-oxazolin-5-one (450 μmol) in acetonitrile (1 mL). Then a preformed solution of bis(η$^3$-allyl)di-μ-chlorodipalladium (II) (1.8 mg, 4.9 μmol) and ligand 1 (10.4 mg, 15.1 μmol) in acetonitrile (1 mL) was added via cannula. The reaction mixture was quenched with aqueous phosphate buffer (pH 7, 40 ml) and extracted with CH$_2$Cl$_2$ (3×30 mL). The combined organic layer were dried over Na$_2$SO$_4$ and concentrated in vacuo. The residue was purified by flash chromatography on silica gel eluting with petroleum ether-AcOEt to give an oil of 4-alkyl-4(2'-cyclohexenyl)-2-phenyl-2-oxazolin-5-one.

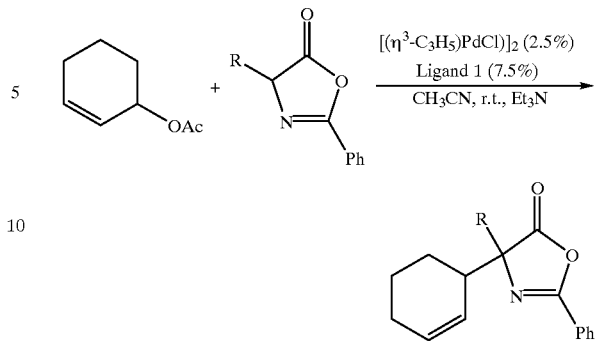

| R | Time | Yield[a] | D.r. (e.e.) |
|---|---|---|---|
| —CH$_3$ (78.8 mg) | 4 h | 90% (45.8 mg) | 8.7:1 (99) (97) |
| —CH$_2$Ph (113.1 mg) | 2 h | 74%[d] (48.9 mg) | 12.4:1 (99) — |
| —CH$_2$CH(CH$_3$)$_2$ (97.8 mg) | 2 h 30' | 77%[b] (45.9 mg) | 13.3:1 (99) — |
| —CH(CH$_3$)$_2$ (91.5 mg)[c] | 6 h | 91% (51.4 mg) | >19:1 (95) — |

[a]Mixture yield;
[b]Major isomer yield,
[c]Racemic ligand 1,
[d]In CH$_2$Cl$_2$ 74% yield 4.21(98):1(96).

(1'S, 4S)-4-Benzyl-4(2'-cyclohexenyl)-2-phenyl-2-oxazolin-5-one: Petroleum ether—AcOEt (95:5) for chromatography. Enantiomeric excess was determined by chiral HPLC (Chiracel® OD column, heptane/2-propenyl 99.9:0.1), t$_R$=13.0 (1'S, 4S), 15.3 (1'R, 4R). [α]$_D$=−221.8 (c=1.45, CH$_2$Cl$_2$, for 99.1% e.e.). Oil. IR (neat film from CDCl$_3$): 3063, 3031, 2930, 2861, 2838, 1815, 1655, 1603, 1581, 1495, 1452, 1320, 1293, 1103, 1055, 1026, 967, 889, 873, 778 cm$^{-1}$. $^1$H NMR (300 MHz, CDCl$_3$) δ: 7.82–7.80 (m, 2H), 7.48 (m, 1H), 7.40–7.35 (m, 2H), 7.17–7.09 (m, 5H), 5.85 (m, 1h), 5.60 (m, 1H), 3.33 (d, J=13.2 Hz, 1H), 3.18 (d, J=13.2 Hz, 1H), 2.83 (m, 1H), 2.08–1.99 (m, 3H), 1.88 (m, 1H), 1.71–1.52 (m, 2H). $^{13}$C NMR (75.5 MHz, CDCl$_3$) δ: 179.4, 159.6, 134.6, 132.41 131.3, 130.3, 128.6, 128.1, 127.8, 127.1, 125.9, 124.9, 77.4, 42.7, 40.4, 24.8, 23.8, 21.5. Anal. Calcd for C$_{22}$H$_{21}$NO$_2$; C, 79.73; H, 6.39; N, 4.23. Found: C, 79.79; HI 6.35; N, 4.23.

(1'S, 4R)-4-Benzyl-4(2'-cyclohexenyl)-2-phenyl-2-oxazolin-5-one: Petroleum ether-AcOEt (95:5) for chromatography. Enantiomeric excess was determined by chiral HPLC (Chiracel® OD column, heptane/2-propanol 99.9:0.1), t$_R$=15.8 (1'R, 4S), 19.6 (1'S, 4R). [α]$_D$=+37.7 (c=0.71, CH$_2$Cl$_2$ for 98.7% e.e.). Oil. IR (neat film from CDCl$_3$): 3063, 3031, 2931, 2860, 1814, 1654, 1603, 1581, 1495, 1451, 1321, 1293, 1104, 1055, 1039, 966, 884, 778 cm$^{-1}$. $^1$H NMR (300 MHz, CDCl$_3$) δ: 7.85–7.82 (m, 2H), 7.51 (m, 1H), 7.43–7.27 (m, 2H), 7.18–7.10 (m, 5H), 5.92 (m, 1H), 5.74 (m, 1H), 3.36 (d, J=13.2 Hz, 1H), 3.23 (d, J=13.2 Hz, 1H), 2.82 (m, 1H), 2.04–1.98 (m, 2H), 1.96–1.82 (m, 2H), 1.69–1.52 (m, 2H). $^{13}$C NMR (75.5 MHz, CDCl$_3$) δ: 179.1, 160.1, 134.5, 132.5, 131.6, 130.3, 128.7, 128.1, 127.9, 127.1, 125.7, 124.3, 77.3, 42.0, 40.6, 24.8, 23.6, 21.6. Anal. Calcd for C$_{22}$H$_{21}$NO$_2$; C, 79.73; H, 6.39; N, 4.23. Found: C, 79.62; H, 6.26; N, 4.17.

(1'S, 4S)-4(2'-Cyclohexenyl)-4-isobutyl-2-phenyl-2-oxazolin-5-one (major isomer): Petroleum ether-AcOEt (97:3) for chromatography. Diastereomeric excess was determined by HPLC (Microsorb® Si 80-125-C5, flow 2 mL/min, 254 nm, heptane/AcOEt 98:2, $t_R$(major)=4.1, $t_R$(minor)=4.9). Enantiomeric excess was determined by chiral HPLC (Chiracel® AD column, heptane/2-propenyl 99.9:0.1), $t_R$=6.9 (1'S, 4S), 7.8 (1'R, 4R). $[\alpha]_D$=−108.4 (c=1.20, $CH_2Cl_2$). Oil. IR (neat film from $CDCl_3$): 3032, 2956, 2871, 1814, 1654, 1581, 1495, 1451, 1320, 1290, 1156, 1098, 1037, 1023, 959, 882, 778, 705, 692, 668 $cm^{-1}$. $^1H$ NMR (300 MHz, $CDCl_3$) δ: 8.02–7.99 (m, 2H), 7.57 (m, 1H), 7.51–7.46 (m, 2H), 5.85 (m, 1H), 5.59 (m, 1H), 2.63 (m, 1H), 2.09–1.80 (m, 6H), 1.63–1.44 (m, 3H), 0.89 (d, J=6.6 Hz, 3H), 0.85 (d, J=6.6 Hz, 3H). $^{13}C$ NMR (75.5 MHz, $CDCl_3$) δ: 180.8, 159.4, 132.5, 131.51 128.8, 128.0, 126.2, 124.8, 75.5, 44.0, 43.0, 24.8, 24.0, 23.6, 23.1, 21.6. Anal. Calcd for $C_{19}H_{23}NO_2$; C, 76.74; H, 7.79; N, 4.71. Found: C, 76.75; H, 7.95; N, 4.58.

(1'S, 4R)-4(2'-Cyclohexenyl)-4-isobutyl-2-phenyl-2-oxazolin-5-one (minor isomer): Petroleum ether-AcOEt (97:3) for chromatography. An analytical sample was purified by semipreparative HPLC (Microsorb® Si 80- 199-C5, flow 2 mL/min, 254 nm, heptane/AcOEt 98:2). Oil. IR (neat film from $CDCl_3$): 2925, 2853, 1814, 1654, 1581, 1451, 1320, 1290, 1056, 1037, 1024, 957, 882, 778, 702 $cm^{-1}$. $^1H$ NMR (300 MHz, $CDCl_3$) δ: 8.04–8.01 (m, 2H), 7.59 (m, 1H), 7.56–7.47 (m, 2H), 5.85 (m, 1H), 5.56 (m, 1H), 5.56 (m, 1H), 2.63 (m, 1H), 2.10–1.79 (m, 6H), 1.65–1.45 (m, 3H), 0.90 (d, J=6.6 Hz, 3H), 0.85 (d, J=6.6 Hz, 3H). $^{13}C$ NMR (75.5 MHz, $CDCl_3$) δ: 180.4, -, 132.7, 131.6, 128.9, 128.1, -, 124.3, 75.3, 43.2, 43.0, 24.8, 24.1, 23.0, 23.0, 21.7.

4(2'-Cyclohexenyl)-4-isopropyl-2-phenyl-2-oxazolin-5-one (single isomer): Petroleum ether-AcOEt (98:2) for chromatography. Oil. IR (neat film from $CDCl_3$): 3032, 2969, 2937, 2878, 1813, 1655, 1581, 1494, 1470, 1451, 1389, 1321, 1292, 1073, 1040, 1022, 944, 879, 780, 706, 692, 670 $cm^{-1}$. $^1H$ NMR (300 MHz, $CDCl_3$) δ: 8.02–7.99 (m, 2H), 7.57 (m, 1H), 7.54–7.45 (m, 2H), 5.84 ((m, 1H), 5.52 (m, 1H), 2.84 (m, 1H), 2.44 (hp, J=6.8 Hz, 1H), 2.01–1.95 (m, 2H), 1.89–1.78 (m, 2H), 1.61–138 (m, 2H), 1.01 (d, J=6.8 Hz, 3H), 0.99 (d, J=6.8 Hz, 3H). $^{13}C$ NMR (75.5 MHz, $CDCl_3$) δ: 179.8, 159.9, 132.5, 131.3, 128.8, 128.0, 126.0, 124.5, 79.1, 39.4, 31.2, 24.8, 23.9, 21.6, 16.7, 16.3. Anal. Calcd for $C_{18}H_{21}NO_2$: C, δ; 76.30; H, 7.47; N, 4.94. Found: C, 76.56; H. 7.47; N, 5.00.

EXAMPLE 5

Asymmetric Alkylation of 2-Cyclopentenyl Acetate or Tert-butyl 2-Cyclopentenyl Carbonate with 4-Benzyl-2-phenyl-2-oxazolin-5-one.

2-Cyclopentenyl acetate (25.2 mg, 200 μmol) or tert-butyl 2-cyclopentenyl carbonate (36.8 mg, 200 μmol) was added to a solution of triethylamine (56 μL, 400 μmol) and 4-benzyl-2-phenyl-2-oxazolin-5-one (113.1 mg, 450 μmol) in acetonitrile (1 mL). Then a preformed solution of bis($\eta^3$-allyl)di-μ-chlorodipalladium (II) (1.8 mg, 4.9 μmol) and ligand 1 (10.4 mg, 15.1 μmol) in acetonitrile (1 mL) was added via cannula. After 3 hours the reaction mixture was quenched with aqueous phosphate buffer (pH 7, 40 ml) and extracted with $CH_2Cl_2$ (3×30 mL). The combined organic layer were dried over $Na_2SO_4$ and concentrated in vacuo. The residue was purified by flash chromatography on silica gel eluting with petroleum ether-AcOEt (97:3) to give two fractions: the first one was the major isomer, the second one was a mixture of 4-benzyl-2-phenyl-2-oxazolin-5-one and the minor isomer that could be partially separated.

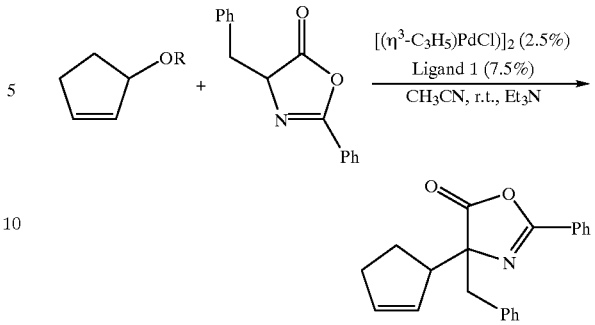

| R | Yield[a] | D.r.[b] (e.e.)[c] | $[\alpha]_D$[d] |
|---|---|---|---|
| —Ac | 71% (45.0 mg) | 5.4:1 (93) — | −290.7 (c = 0.99, $CH_2Cl_2$) |
| —Boc | 69% (43.8 mg) | 5.4:1 (95) — | −301.5 (c = 0.98, $CH_2Cl_2$) |

[a]Isolaled major isomer;
[b]Determined by H-NMR;
[c]Determined by chiral HPLC,
[d]Major isomer.

4-Benzyl-4(2'-cyclopentenyl)-2-phenyl-2-oxazolin-5-one (major isomer): Oil. Enantiomeric excess was determined by chiral HPLC (Chiracel® OD column, heptane/2-propanol 99.9:0.1), $t_R$ (major)=15.3, $t_R$ (minor)=22.4. IR (neat film from $CDCl_3$): 3062, 3032, 2926, 2850, 1814, 1655, 1603, 1580, 1496, 1452, 1320, 1291, 1234, 1177, 1159, 1094, 1048, 1009, 972, 888, 778, 700 $cm^{-1}$. $^1H$ NMR (300 MHz, $CDCl_3$) δ: 7.82–7.79 (m, 2H), 7.49 (m, 1H), 7.41–7.36 (m, 2H), 7.18–7.10 (m, 5H), 5.90 (m, 1H), 5.60 (m, 1H), 3.55 (m, 1H), 3.31 (d, J=13.4 Hz, 1H), 3.19 (d, J=13.4 Hz, 1H), 2.50–2.27 (m, 2H), 2.19–1.98 (m, 2H). $^{13}C$ NMR (75.5 MHz, $CDCl_3$) δ: 179.4, 159.7, 135.3, 134.7, 132.4, 130.2, 128.6, 128.2, 128.1, 127.8, 127.1, 125.9, 77.2, 53.2, 41.5, 32.2, 24.9. Anal. Calcd for $C_{22}H_{21}NO_2$; C, 79.47; H, 6.03; N, 4.41. Found: C, 79.84; H, 6.08; N, 4.28.

4-Benzyl-4(2'-cyclospentenyl)-2-phenyl-2-oxazolin-5-one (minor isomer): Oil. IR (neat film from $CH_2Cl_2$): 3062, 3032, 2925, 2851, 1814, 1654, 1603, 1581, 1495, 1452, 1320, 1292, 1097, 1060, 1049, 1013, 968, 990, 779, 700 $cm^{-1}$. $^1H$ NMR (300 MHz, $CDCl_3$) δ: 7.86–7.83 (m, 2H), 7.52 (m, 1H), 7.44–7.39 (m, 2H), 7.18–7.11 (m, 5H), 5.97 (m, 1H), 5.75 (m, 1H), 3.36 (m, 1H), 3.30 (d, J=13.3 Hz, 1H), 3.23 (d, J=13.3 Hz, 1H), 2.50–2.28 (m, 2H), 2.15–1.90 (m, 2H). $^{13}C$ NMR (75.5 MHz, $CDCl_3$) δ: 179.1, 160.1, 135.5, 134.7, 132.5, 130.3, 128.7, 128.2, 128.2, 127.9, 127.1, 125.8, 77.0, 52.6, 41.4, 32.4, 24.2. Calcd for $C_{21}H_{19}NO_2$: 317.1416. Found: 317.1413.

EXAMPLE 6

Asymmetric Alkylation of Allylic Acetate with 4-Benzyl-2-phenyl-2-oxazolin-5-one.

Allyl acetate (21.6 μL, 200 μmol) was added to a solution of triethylamine (56 μL, 400 μmol) or pentamethylguanidine (51.7 mg, 400 μmol) and 4-benzyl-2-phenyl-2-oxazolin-5-one (450 μmol) in acetonitrile (1 mL). Then a preformed solution of bis($\eta^3$-allyl)di-μ-chlorodipalladium (II) (1.8 mg, 4.9 μmol) and ligand 1 (10.4 mg, 15.1 μmol) in acetonitrile (1 mL) was added via cannula. The reaction mixture was quenched with aqueous phosphate buffer (pH 7, 40 ml) and extracted with $CH_2Cl_2$ (3×30 mL). The combined organic layer was dried over $Na_2SO_4$ and concentrated in vacuo. The residue was purified by flash chromatography on silica gel eluting with petroleum ether-AcOEt (95:5) to give 4-allyl-4-benzyl-2-phenyl-2-oxazolin-5-one.

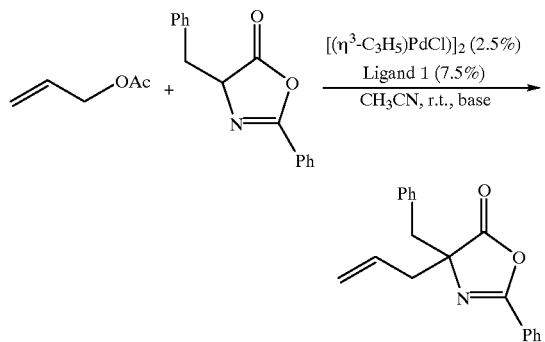

| Base | Time | Yield[a] | E.e.[b] | $[\alpha]_D$ |
|---|---|---|---|---|
| $Et_3N$ | 2 h 30' | 98% (57.5 mg) | 40% | −31.1 (c = 1.10, $CH_2Cl_2$) |
| Pentamethyl-guanidine | 5 h | 70%[d] (45.0 mg) | 30% | −25.4 (c = 0.98, $CH_2Cl_2$) |

[a]Not including the catalyst;
[b]Determined by chiral HPLC.

4-Allyl-4-benzyl-2-phenyl-2-oxazolin-5-one: Enantiomeric excess was determined by chiral HPLC (Chiracel® OD column, heptane/2-propenyl 99.9:0.1), $t_R$ (major)=14.3, $t_R$ (minor)=17.4. IR (neat film from $CH_2Cl_2$): 3064, 3032, 2922, 1817, 1656, 1603, 1581, 1495, 1452, 1436, 1321, 1292, 1176, 1137, 1087, 1046, 977, 929, 890, 780, 738, 700, 665 $cm^{-1}$. $^1$H NMR (300 MHz, $CDCl_3$) δ: 7.86–7.83 (m, 2H), 7.52 (m, 1H), 7.41 (m, 2H), 7.18–7.13 (m, 5H), 5.68 (m, 1H), 5.24–5.10 (m, 2H), 3.24 (d, J=13.4 Hz, 1H), 3.16 (d, J=13.4 Hz, 1H), 2.80–2.67 (m, 2H). $^{13}$C NMR (75.5 MHz, $CDCl_3$) δ: 179.3, 160.0, 134.4, 132.6, 130.8, 103.2, 128.7, 128.2, 127.9, 127.3, 125.7, 120.6, 74.8, 43.1, 41.3. Anal. Calcd for $C_{19}H_{17}NO_2$; C, 78.33; H, 5.88; N, 4.81. Found: C, 78.25; H, 5.94; N, 4.81.

EXAMPLE 7

Asymmetric Alkylation of 3,3-Diacetoxy-1-phenyl-1-propene with 4-Alkyl-2-phenyl-2-oxazonlin-5-one. General Procedure.

A solution (1.0 mL) of 4-alkyl-2-phenyl-2-oxazolin-5-one (450 μmol) was added to NaH (95% in oil, 10.1 mg, 400 μmol) at −78° C. and warmed to room temperature. When the bubbling stopped, a solution (0.5 mL) of bis($\eta^3$-allyl) di-μ-chlorodipalladium (II) (1.8 mg, 4.9 μmol) and ligand 1 (10.4 mg, 15.1 μmol). Finally, another solution (1.0 mL) of 3,3 diacetoxy-1-phenylpropene (46.9 mg, 200 μmol) was added at the desired temperature. The reaction mixture was quenched with aqueous phosphate buffer (pH 7, 40 mL) and extracted with $CH_2Cl_2$ (3×30 mL). The combined organic layer was dried over $Na_2SO_4$ and concentrated in vacuo. The residue was purified by flash chromatography on silica gel eluting with petroleum ether-AcOEt.

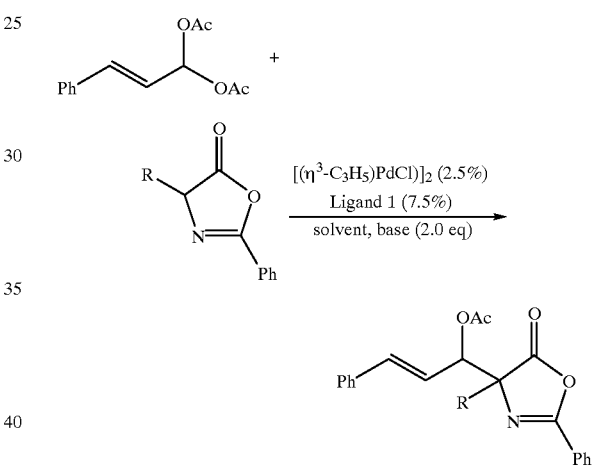

| R | Sol.(T) | Time | Base | Yield[a] | E.e.[b] | D.r.[c] | $[\alpha]_D^e$ |
|---|---|---|---|---|---|---|---|
| —$CH_3$ 78.8 mg | $CH_2Cl_2$ r.t. | 18 h | $Et_3N$ | 73% (50.9 mg) 16% (11.4 mg) | 83% 40% | 4.4:1 | −193.5 (2.84) −37.9 (0.86) |
| —$CH_3$ 78.8 mg | THF r.t. | 18 h | NaH | 38% (26.4 mg) 6% (4.5 mg) | 98% 91% | —:— | −221.0 (2.20) −82.2 (0.27) |
| —$CH_3$ 78.8 mg | DME r.t. | 5 h | NaH | 60% (42.1 mg) 9% (6.4 mg) | 99% 96% | 6.6:1 | −227.7 (4.21) −92.6 (0.64) |
| —$CH_2Ph$ 113.1 mg | DME r.t. | 5 h | NaH | 67% (57.2 mg) 7% (6.3 mg) | 98% 94% | 7.8:1 | −283.5 (2.67) +19.1 (0.62) |
| —$CH_2Ph$ 113.1 mg | DME 0–5° C. | 24 h | NaH | 75% (64.2 mg) 6% (4.9 mg) | 99% 96% | 9.7:1 | −290.1 (1.08) +21.5 (0.22) |
| —$CH_2Ph$ 113.1 mg | DME −20° C. | 24 h | NaH | 67% (56.7 mg) 5% (5.9 mg) | 99% 98% | 11.2:1 | −289.3 (1.52) +25.5 (0.46) |
| -Isobutyl 97.8 mg | DME 0–5° C. | 3 h | NaH | 91% (71.1 mg) 6% (4.7 mg) | 99% 95% | 15:1 | −235.2 (1.02) −40.5 (0.41) |

-continued

| R | Sol.(T) | Time | Base | Yield[a] | E.e.[b] | D.r.[c] | [α]$_D$[e] |
|---|---------|------|------|----------|---------|---------|------------|
| -Isopropyl 91.5 mg | DME 0–5° C. | 2 h | NaH | 88% (66.4 mg) 4% (4.4 mg)[d] | 99% — | >19:1 — | −208.0 (1.02) — |

[a]Isolated yield;
[b]Determined by chiral HPLC;
[c]Determined by H-NMR;
[d]2% of the other regioisomer;
[e]Conc. in $CH_2Cl_2$.

(E, 1'R, 4S)-4-(1'-Acetoxy-3'-phenyl-2'-propenyl)-4-methyl-2-phenyl-2-oxazolin-5-one: (major isomer, first fraction). Petroleum ether-AcOEt (9:1) for chromatography. M.p.: 138–139° C. (isopropanol). Enantiomeric excess was determined by chiral HPLC (Chiracel® OD column, heptane/2-propanol 99:1), $t_R$(minor)=11.6, $t_R$(major)=13.7. IR(neat film from $CH_2Cl_2$): 3601, 3029, 2985, 2936, 1827, 1749, 1656, 1581, 1495, 1451, 1371, 1322, 1294, 1223, 1179, 1092, 1071, 1007, 971, 904, 781, 743, 694 cm$^{-1}$. $^1$H NMR (300 MHz, $CDCl_3$) δ: 8.10–8.07 (m, 2H), 7.65–7.45 (m, 5H), 7.38–7.26 (m, 3H), 6.88 (d, J=15.9 Hz, 1H), 6.32 (dd, J=15.9, 8.8 Hz, 1H), 5.66 (d, J=8.8 Hz, 1H), 1.96 (s, 3H), 1.50 (s, 3H). $^{13}$C NMR (75.5 MHz, $CDCl_3$) δ: 178.9, 169.4, 161.3, 138.4, 135.7, 133.0, 128.9, 128.7, 128.6, 128.2, 127.1, 125.8, 121.3, 77.6, 72.2, 20.8, 20.3. Anal. Calcd for $C_{21}H_{19}NO_4$: C, 72.19; H, 5.48; N, 4.01. Found: C, 72.32; H. 5.62; N, 4.01.

(E, 1'R, 4R)-4-(1'-Acetoxy-3'-phenyl-2'-propenyl)-4-methyl-2-phenyl-2-oxazolin-5-one (minor isomer, second fraction). Petroleum ether-AcOEt (9:1) for chromatography. M.p.: 142–144° C. Enantiomeric excess was determined by chiral HPLC (Chiracel® OD column, heptane/2-propanol.99:1), $t_R$ (major)=12.8, $t_R$ (minor)=15.6. IR (neat film from $CH_2Cl_2$): 3061, 3029, 2935, 1822, 1748, 1655, 1581, 1494, 1451, 1372, 1322, 1294, 1226, 1150, 1115, 1094, 1072, 1008, 971, 906, 882, 782, 746, 694 cm$^{-1}$. $^1$H NMR (300 MHz, $CDCl_3$) δ: 8.03–8.00 (m, 2H), 7.63–7.42 (m, 5H), 7.36–7.28 (m, 3H), 6.81 (d, J=15.9 Hz, 1H), 6.36 (dd, J=15.9, 8.9 Hz, 1H), 5.71 (d, J=8.9 Hz, 1H), 1.94 (s, 3H), 1.53 (s, 3H). $^{13}$C NMR (75.5 MHz, $CDCl_3$) δ: 178.1, 169.5, 161.5, 137.6, 135.7, 133.1, 129.0, 128.7, 128.7, 128.1, 127.1, 125.6, 120.5, 77.3, 71.7, 20.8, 20.3. Anal. Calcd for $C_{21}H_{19}NO_4$; C, 72.19; H, 5.48; N, 4.01. Found: C, 72.38; H, 5.57; N, 4.00.

(E, 1'R, 4S)-4-(1-Acetoxy-3'-phenyl-2'-propenyl)-4-benzyl-2-phenyl-2-oxazolin-5-one (major isomer, first fraction). Petroleum ether-AcOEt (9:1) for chromatography on silica gel (2% $Et_3N$). M.p.: 138–140° C. (isopropanol). Enantiomeric excess was determined by chiral, HPLC (Chiracel® OD column, heptane/2-propanol 99:1), $t_R$ (minor)=17.2, $t_R$ (major)=21.5. IR (neat film from $CDCl_3$): 3031, 1820, 1748, 1655, 1496, 1451, 1370, 1322, 1293, 1227, 1053, 1023, 971, 693 cm$^{-1}$. $^1$H NMR (300 MHz, $CDCl_3$) δ: 7.91–7.88 (m, 2H), 7.57–7.27 (m, 8H), 7.14–7.11 (m, 5H), 6.95 (d, J=16.0 Hz, 1H), 6.42 (dd, J=16.0, 8.9 Hz, 1H), 5.84 (d, J=8.9 Hz, 1H), 3.21 (d, J=13.3 Hz, 1H), 3.12 (d, J=13.3 Hz, 1H), 1.96 (s, 3H). $^{13}$C NMR (75.5 MHz, $CDCl_3$) δ: 177.6, 169.41 161.31 138.4, 135.7, 133.3, 132.8, 130.3, 128.7, 128.2, 128.1, 127.4, 127.1, 125.6, 121.6, 77.5, 77.2, 39.9, 20.9. Anal. Calcd for $C_{27}H_{23}NO_4$; C, 76.22; H, 5.45; N, 3.29. Found; C, 76.37; H, 5.30; N., 3.24.

(E, 1'R, 4R)-4-(1'-Acetoxy-3'-phenyl-2'-propenyl)-4-benzyl-2-phenyl-2-oxazolin-5-one (minor isomer, second fraction). Petroleum ether-AcOEt (9:1) for chromatography on silica gel (2% $Et_3N$). Oil. Enantiomeric excess was determined by chiral HPLC (Chiracel® AD column, heptane/2-propanol 9:1), $t_R$ (major)=7.6, $t_R$ (minor)=13.7. IR (neat film from $CDCl_3$): 3031, 1817, 1748, 1655, 1496, 1451, 1371, 1322, 1293, 1226, 1051, 988, 694 cm$^{-1}$. $^1$H NMR (300 MHz, $CDCl_3$) δ: 7.87–7.84 (m, 2H), 7.57–7.30 (m, 8H), 7.18–7.13 (m, 5H), 6.84 (d, J=15.9 Hz, 1H), 6.47 (dd, J=15.9, 9.0 Hz, 1H), 5.87 (d, J=9.0 Hz, 1H), 3.25 (d, J=13.5 Hz, 1H), 3.19 (d, J=13.5 Hz, 1H), 1.96 (s, 3H). $^{13}$C NMR (75.5 MHz, $CDCl_3$) δ: 177.0, 169.5, 161.5, 137.8, 135.7, 133.5, 132.9, 130.4, 128.8, 128.3, 128.0, 127.4, 127.1, 125.4, 120.6, 77.2, 76.9, 39.9, 20.8. HRMS Calcd for $C_{27}H_{24}NO_4$ (M+1); 426.1705. Found: 426.1720.

(E, 1'R, 4S)-4-(1'-Acetoxy-3'-phenyl-2'-propenyl)-4-isobutyl-2-phenyl-2-oxazolin-5-one (major isomer, first fraction). Petroleum ether-AcOEt (95.5 to 9:1) for chromatography. M.p.: 164–165° C. (racemic, heptane/2-propanol, 9:1). Enantiomeric excess was determined by chiral HPLC (Chiracel® AD column, heptane/2-propanol 99.5:0.5), $t_R$ (major)=15.7, $t_R$ (minor)=19.1. IR (neat film from $CH_2Cl_2$): 3061, 3028, 2959, 2873, 1819, 1747, 1655, 1601, 1580, 1495, 1451, 1370, 1321, 1295, 1222, 1159, 1046, 1023, 969, 917, 885, 779, 744, 708, 693, 669 cm$^{-1}$. $^1$H NMR (300 MHz, $CDCl_3$) δ: 8.11–8.01 (m, 2H), 7.63 (m, 1H), 7.56–7.46 (m, 4H), 7.38–7.26 (m, 3H), 6.86 (d, J=15.9 Hz, 1H), 6.30 (dd, J=15.9, 8.8 Hz, 1H), 5.61 (d, J=8.8 Hz, 1H), 1.95 (dd, J=14.0, 7.1 Hz, 1H), 1.95 (s, 3H), 1.79' (dd, J=14.0, 7.1 Hz, 1H), 1.57 (m, 1H), 0.85 (m, J=6.5 Hz, 3H), 0.84 (m, J=6.6 Hz, 3H). $^{13}$C NMR (75.5 MHz, $CDCl_3$) δ: 179.2, 169.3, 161.3, 138.4, 135.8, 133.0, 128.9, 128.7, 128.6, 128.3, 127.1, 125.9, 121.7, 78.0, 75.9, 42.0, 24.5, 23.8, 23.0, 20.9. Anal. Calcd for $C_{24}H_{25}NO_4$; C, 73.64; H, 6.44; N, 3.58. Found: C, 73.44; H, 6.19; N, 3.68.

(E, 1'R, 4R)-4-(1'-Acetoxy-3'-phenyl-2'-propenyl)-4-isobutyl-2-phenyl-2-oxazolin-5-one (minor isomer, second fraction). Petroleum ether-AcOEt (95:5 to 9:1) for chromatography. Oil. Enantiomeric excess was determined by chiral HPLC (Chiracel® AD column, heptane/2-propanol 95:5), $t_R$ (major)=8.2, $t_R$ (minor)=10.0. IR (neat film from $CDCl_3$): 3062, 3029, 2960, 2927, 2873, 1818, 1749, 1655, 1602, 1580, 1495, 1451, 1371, 1322, 1293, 1225, 1040, 1025, 982, 912, 885, 782, 745, 702 cm$^{-1}$. $^1$H NMR (300 MHz, $CDCl_3$) δ: 8.04–8.02 (m, 2H), 7.61 (m 1H), 7.54–7.44 (m, 4H), 7.38–7.30 (m, 3H), 6.80 (d, J=15.9 Hz, 1H), 6.39 (dd, J=15.9, 9.1 Hz, 1H), 5.70 (d, J=9.1 Hz, 1H), 1.94 (dd. J=13.8, 4.8 Hz, 1H), 1.88 (s, 3H), 1.79 (dd, J=13.8, 4.8 Hz, 1H), 1.67 (m, 1H), 0.89 (m, J=6.5 Hz, 3H), 0.83 (m, J=6.5 Hz, 3H). $^{13}$C NMR (75.5 MHz, $CDCl_3$) δ: 178.5, 169.4, 161.4, 137.6, 135.7, 133.0, 129.0, 128.7, 128.1, 127.1, 125.7, 120.3, 77.6, 75.0, 42.4, 24.7, 24.0, 22.6, 20.8. HRMS (CI): Calcd for $C_{22}H_{12}NO_3$ (M-COCH$_3$): 348.1600. Found: 348.1587.

(E, 1'R, 4S)-4-(1'-Acetoxy-3'-phenyl-2'-propenyl)-4-isopropsyl-2-phenyl-2-oxazolin-5-one (major isomer, first fraction). Petroleum ether-AcOEt (95:5 to 9:1) for chromatography. Oil. Enantiomeric excess was determined by chiral HPLC (Chiracel® OD column, heptane/2-propanol 99.8:0.2), $t_R$ (major)=22.4, $t_R$ (minor)=27.5. IR (neat film from CDCl$_3$): 3061, 3028, 2973, 2881, 1814, 1747, 1656, 1602, 1580, 1495, 1451, 1371, 1321, 1294, 1229, 1177, 1161, 1087, 1044, 1022, 969, 939, 913, 883, 782, 750, 733, 693 cm$^{-1}$. $^1$H NMR (300 MHz, CDCl$_3$) δ: 8.10–8.07 (m, 2H), 7.61 (m, 1H), 7.55–7.49 (m, 2H), 7.46–7.43 (m, 2H), 7.36–7.26 (m, 3H), 6.91 (d, J=16.1 Hz, 1H), 6.33 (dd, J=16.1, 8.8 Hz, 1H), 5.92 (d, J=8.8 Hz, 1H), 2.29 (hp, 1H), 1.96 (s, 3H), 1.18 (d, J=6.9 Hz, 3H), 0.91 (d, J=6.9 Hz, 3H). $^{13}$C NMR (75.5 MHz, CDCl$_3$) δ: 177.4, 169.5, 161.4, 137.8, 135.8, 132.9, 128.9, 128.7, 128.6, 128.2, 127.0, 125.8, 121.8, 78.9, 75.3, 31.8, 20.9, 17.0, 15.5. Anal. Calcd for C$_{23}$H$_{23}$NO$_4$; C, 73.19; H, 6.14; N. 3.71. Found: C, 73.33; H, 5.94; N, 3.56.

(E, 1'R, 4R)-4-(1'-Acetoxy-3'-phenyl-2'-propenyl)-4-isopropyl-2-phenyl-2-oxazolin-5-one (minor isomer, third fraction). Petroleum ether-AcOEt (95:5 to 9:1) for chromatography. Oil impurified with the other regioisomer. $^1$H NMR (300 MHz, CDCl$_3$) δ: 8.06–8.03 (m, 2H), 7.61 (m, 1H), 7.55–7.44 (m, 4H), 7.38–7.28 (m, 3H), 6.88 (d, J=15.8 Hz, 1H), 6.49 (dd, J=15.8, 9.3 Hz, 1H), 5.87 (d, J=9.3 Hz, 1H), 2.30 (hp, 1H), 1.87 (s, 3H), 1.16 (d, J=6.7 Hz, 3H), 0.85 (d, J=6.7 Hz, 3H).

4-(3'-Acetoxy-1'-phenyl-2'-prospenyl)-4-isopropyl-2-phenyl-2-oxazolin-5-one (second fraction, only one diastereoisomer). Petroleum ether-AcOEt (95:5 to 9:1) for chromatography. Oil impurified with the other regioisomer. $^1$H NMR (300 MHz, CDCl$_3$) δ: 7.87–7.85 (m, 2H), 7.61–7.44 (m, 6H), 7.17–7.10 (m, 3H), 6.07 (dd, J=12.6, 10.7 Hz, 1H), 3.99 (d, J=10.7 Hz, 1H), 2.38 (hp, 1H), 2.13 (s, 3H), 1.27 (d, J=6.9 Hz, 3H), 0.86 (d, J=6.9 Hz, 3H).

EXAMPLE 8

Asymmetric Alkylation of 1,1-Diacetoxy-2-hexene with 4-Alkyl-2-phenyl-2-oxazolin-5-one. General Procedure.

A solution of 4-alkyl-2-phenyl-2-oxazolin-5-one (450 μmol) was added to NaH (95% in oil, 10.1 mg, 400 μmol) at −78° C. and warmed to room temperature in DME (1.0 mL). When the bubbling stopped, a solution of bis(η$^3$-allyl) di-μ-chlorodipalladium (II) (1.8 mg, 4.9 μmol) and ligand 1 (10.4 mg, 15.1 μmol) in DME (1.5 mL). Finally, 1,1-diacetoxy-2-hexene (40.0 mg, 200 μmol) was added dropwise at 0° C. The reaction mixture was quenched with aqueous phosphate buffer (pH 7, 40 ml) and extracted with CH$_2$Cl$_2$ (3×30 mL). The combined organic layer was dried over Na$_2$SO$_4$ and concentrated in vacuo. The residue was purified by flash chromatography on silica gel eluting with petroleum ether-AcOEt (95:5).

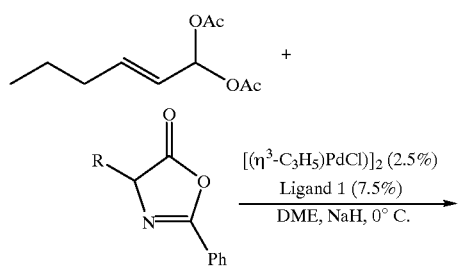

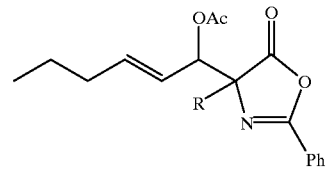

| R | Time | Yield[b] | E.e.[c] | D.r.[a] | [α] |
|---|---|---|---|---|---|
| —CH$_3$ | 6 hr | 22% (13.7 mg) | 86% | 1:1[d] | −71.5 (c = 0.81) |
| (78.8 mg) | | 22% (13.7 mg) | 97% | | −40.9 (c = 0.49) |
| —CH$_2$Ph | 2 hr | 39% (30.4 mg) | 91% | 1.2:1 | −161.2 (c = 1.90) |
| (113.1 mg) | | 33% (25.7 mg) | 97% | | +90.4 (c = 1.67) |

[a]Determined by H-NMR;
[b]Isolated yield;
[c]Determined by chiral HPLC;
[d]The other regioisomer was obtained in 20% (12.5 mg) yield and d.r.(e.e.) 3.1(71%):1(65%).

4-(1'-Acetoxy-2'-hexenyl)-4-benzyl-2-phenyl-2-oxazolin-5-one (major isomer, first fraction): Oil. Enantiomeric excess was determined by chiral HPLC (Chiracel® OD column, heptane/2-propanol 99.5:0.5), $t_R$ (minor)=10.9, $t_R$ (major)=15.5. IR (neat film from CDCl$_3$): 3064, 3033, 2959, 2929, 2872, 1822, 1750, 1656, 1602, 1581, 1496, 1452, 1370, 1322, 1293, 1229, 1120, 1054, 1024, 973, 894, 779, 736, 702 cm$^{-1}$. $^1$H NMR (300 MHz, CDCl$_3$) δ: 7.88–7.85 (m, 2H), 7.54 (m, 1H), 7.46–7.41 (m, 2H), 7.14–7.10 (m, 5H), 6.07 (m, 1H), 5.72–5.61 (m, 2H), 3.18 (d, J=13.4 Hz, 1H), 3.09 (d, J=13.4 Hz, 1H), 2.16–2.09 (m, 2H), 1.96 (s, 3H), 1.45 (m, 1H), 0.91 (t, J=7.3 Hz, 3H). $^{13}$C NMR (75.5 MHz, CDCl$_3$) δ: 177.8, 169.4, 161.1, 140.8, 133.5, 132.7, 130.3, 128.7, 128.2, 128.0, 127.4, 125.7, 123.0, 77.4, 77.3, 39.9, 34.3, 21.8, 20.8, 13.5. Anal. Calcd for C$_{24}$H$_{25}$NO$_4$; C, 73.64; H, 6.44; N, 3.58. Found: C, 73.45; H, 6.19; N, 3.37.

4-(1'-Acetoxy-2'-hexenyl)-4-benzyl-2-phenyl-2-oxazolin-5-one (minor isomer, second fraction): Oil. Enantiomeric excess was determined by chiral HPLC (Chiracel® OD column, heptane/2-propanol 99.5:0.5), $t_R$ (major)=10.7, $t_R$ (minor)=14.9. IR (neat film from CDCl$_3$): 3064, 3033, 2959, 2930, 2872. 1818, 1750, 1655, 1602, 1581, 1496, 1452, 1371, 1321, 1293, 1228, 1045, 1022, 985, 892, 779, 745, 700 cm$^{-1}$. $^1$H NMR (300 MHz, CDCl$_3$) δ: 7.85–7.82 (m, 2H), 7.53 (m, 1H), 7.44–7.39 (m, 2H), 7.17–7.11 (m, 5H), 5.96 (m, 1H), 5.75–5.67 (m, 2H), 3.20 (d, J=13.4 Hz, 1H), 3.15 (d, J=13.4 Hz, 1H), 2.13–2.06 (m, 2H), 1.95 (s, 3H), 1.43 (m, 1H), 0.89 (t, J=7.3 Hz, 3H). $^{13}$C NMR (75.5 MHz, CDCl$_3$) δ: 177.0, 169.5, 161.2, 140.2, 133.7, 132.8, 130.3, 128.7, 128.2, 127.9, 127.3, 125.5, 122.0, 76.9, 77.1, 39.8, 34.2, 21.8, 20.9, 13.4. Anal. Calcd for C$_{24}$H$_{25}$NO$_4$; C, 73.64; H, 6.44; N, 3.58. Found: C, 73.56; H, 6.44; N, 3.58.

4-(1'-Acetoxy-2'-hexenyl)-4-methyl-2-phenyl-2-oxazolin-5-one (first fraction): Oil. Enantiomeric excess (86%) was determined by chiral HPLC (Chiracel® OD column, heptane/2-propanol 99.5:0.5), $t_R$ (minor)=8.0, $t_R$ (major)=10.3. IR (neat film from CDCl$_3$): 2960, 2933, 2873, 1828, 1750, 1657, 1452, 1371, 1322, 1294, 1226, 1185, 1007, 973, 904, 781, 744, 701 cm$^{-1}$. $^1$H NMR (300 MHz, CDCl$_3$) δ: 8.06–8.03 (m, 2H), 7.61 (m, 1H), 7.54–7.48 (m, 2H), 6.00 (m, 1H), 5.58 (m, 1H), 5.45 (d, J=8.8 Hz, 1H), 2.13–2.05 (m, 2H), 1.95 (s, 3H), 1.46 (s, 3H), 1.49–1.37 (m, 2H), 0.89 (t, J=7.4 Hz, 3H). $^{13}$C NMR (75.5 MHz, CDCl$_3$) δ: 179.1, 169.4, 161.1, 140.8, 132.9, 128.9, 128.2, 125.9, 122.5, 77.7, 72.1, 34.3, 21.8, 20.9, 20.3, 13.5. HRMS (CI): Calcd for C$_{18}$H$_{22}$NO$_4$ (M+1): 316.1549. Found: 316.1550.

4-(3'-Acetoxy-1'-propenyl-2'-prospenyl)-4-methyl-2-phenyl-2-oxazolin-5-one (second fraction): Mixture of two diastereoisomers: A(major) and B(minor). Diastereomeric and enantiomeric excess were determined by chiral HPLC (Chiracel® OD column, heptane/2-propanol 99.8:0.2), $t_R$ (A, major)=10.6, $t_R$ (A, minor)=12.1, $t_R$ (B, minor)=13.71, $t_R$ (B, major)=18.2. Spectral data of the mixture (only A is shown): IR (neat film from CDCl$_3$): 2960, 2932, 2873, 1822, 1760, 1655, 1582, 1495, 1452, 1371, 1321, 1293, 1220, 1167, 1100, 1069, 1004, 943, 893, 781, 749, 701, 670 cm$^{-1}$. $^1$H NMR (300 MHz, CDCl$_3$) δ: 8.03–8.00 (m, 2H), 7.57 (m, 1H), 7.52–7.47 (m, 2H), 7.21 (d, J=12.6 Hz, 1H), 5.37 (dd, J=12.6, 10.0 Hz, 1H), 2.40 (m, 1H), 2.15 (s, 3H), 1.46 (s, 3H), 1.40–1.14 (m, 4H), 0.82 (t, J=7.1 Hz, 3H). $^{13}$C NMR (75.5 MHz, CDCl$_3$) δ: 181.1, 168.1, 160.2, 138.2, 132.8, 128.9, 128.1, 125.9, 112.6, 72.2, 45.5, 31.9, 22.9, 20.6, 20.2, 13.6. HRMS (CI): Calcd for C$_{18}$H$_{21}$NO$_4$ (M+1); 316.1549. Found. 316.1559.

4-(1'-Acetoxy-2'-hexenyl)-4-methyl-2-phenyl-2-oxazolin-5-one (third fraction): Oil. Enantiomeric excess (97%) was determined by chiral HPLC (Chiracel® OD column, heptane/2-propanol 99.5:0.5), $t_R$ (major)=9.1, $t_R$ (minor)=13.2. IR (neat film from CH$_2$Cl$_2$): 2960, 2933, 2873, 1823, 1750, 1656, 1602, 1582, 1451, 1372, 1322, 1294, 1228, 1131, 1093, 1007, 974, 881, 781, 756, 699 cm$^{-1}$. $^1$H NMR (300 MHz, CDCl$_3$) δ: 8.01–7.99 (m, 2H), 7.60 (m, 1H), 7.52–7.47 (m, 2H), 5.93 (m, 1H), 5.65–5.50 (ml 2H), 2.10–2.02 (m, 2H), 1.93 (s, 3H), 1.49 (s, 3H), 1.47–1.35 (m, 2H), 0.88 (t, J=7.4 Hz, 3H). $^{13}$C NMR (75.5 MHz, CDCl$_3$) δ: 178.2, 169.6, 161.2, 139.9, 133.0, 128.8, 128.1, 125.9, 121.8, 77.4, 71.7, 34.2, 21.8, 20.8, 20.2, 13.4. HRMS (CI): Calcd for C$_{18}$H$_{22}$NO$_4$ (M+1): 316.1549. Found: 316.1555.

It is to be understood that while the invention has been described above in conjunction with preferred specific embodiments, the description and examples are intended to illustrate and not limit the scope of the invention, which is defined by the scope of the appended claims.

It is claimed:

1. A method for preparing enantiomerically enriched compounds comprising:

alkylating an allylic electrophile with a 5-(4H)-oxazolone of the formula

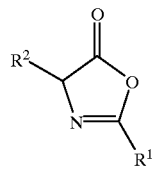

in the presence of a base and a transition metal complex having one or more chiral ligands, wherein $R^1$ is selected from a group consisting of hydrogen, substituted and unsubstituted C$_1$–C$_{20}$ allyls, substituted and unsubstituted C$_1$–C$_{20}$ aryls, and substituted and unsubstituted C$_1$–C$_{20}$ heteroaryls, $R^2$ is an amino acid side-chain, a substituted amino acid side-chain or is selected from a group consisting of substituted and unsubstituted C$_1$–C$_{20}$ alkls, substituted and unsubstituted C$_1$–C$_{20}$ aryls, and substituted and unsubstituted C$_1$–C$_{20}$ heteroaryls, wherein the allylic electrophile is selected from

and

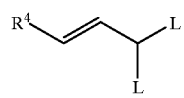

wherein n=1 to 6, $R^4$ is selected from a group consisting of hydrogen, substituted and unsubstituted C$_1$–C$_{20}$ alkyls, substituted and unsubstituted C$_1$–C$_{20}$ aryls, and substituted and unsubstituted C$_1$–C$_{20}$ heteroaryls, and L is an ionizable group, to form 4,4-disubstituted-5(4H)-oxazolones.

2. The method as in claim 1 wherein $R^2$ is an amino acid side-chain or a substituted amino acid side-chain.

3. The method as in claim 1 wherein L is a halide, an ester, a carbonate, or a carboxylate.

4. The method as in claim 1 wherein the transition metal is Pd(0) and the chiral ligand is a bidentate diphosphine with a pair of metal binding moieties of the type —C(=O)—Ar—P—(Ar')$_2$, wherein Ar and Ar' are aromatic substituents.

5. The method as in claim 4 wherein the chiral ligand is of the formula

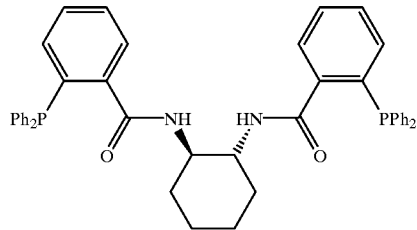

or the opposite enantiomer thereof.

6. The method as in claim 1 wherein $R^3$-L is of the formula

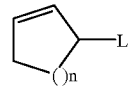

wherein n is 1–6.

7. The method as in claim 6 wherein n=1 and L is acetate.

8. The method as in claim 1 wherein the allylic electrophile is an allylic diacetate of the formula

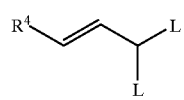

where L is acetate, and where one L group is retained in the product.

9. The method as in claim 8 wherein $R^3$-L is 3,3-diacetoxy-1-phenyl-1-propene.

10. The method as in claims 7, 8, or 9 wherein $R^1$ is phenyl and $R^2$ is an amino acid side-chain or a substituted amino acid side-chain.

11. The method as in claim 1 further comprising transforming said 4,4-disubstituted-5(4H)-oxazolones compounds to enantiomerically enriched α, α-disubstituted amino acids of the formula

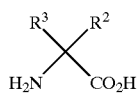

12. The method as in claim 11 wherein the transforming includes hydrolysis or alcoholysis of the heterocyclic ring.

13. An enantiomerically enriched (ee) composition, comprising:

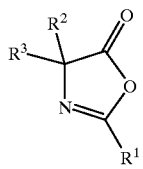

wherein $R^1$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls; $R^2$ is an amino acid side-chain, a substituted amino acid side-chain or is selected from a group consisting of substituted and unsubstituted $C_1$–$C_{20}$ alkyls, substituted and unsubstituted $C_1$–$C_{20}$ aryls, and substituted and unsubstituted $C_1$–$C_{20}$ heteroaryls; and $R^3$ is selected from the group consisting of substituents represented by formulas

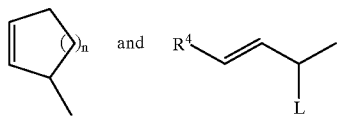

wherein n=1 to 6, $R^4$ is selected from a group consisting of hydrogen, substituted and unsubstituted $C_1$–$C_{20}$ alkyls, substituted and unsubstituted $C_1$–$C_{20}$ aryls, and substituted and unsubstituted $C_1$–$C_{20}$ heteroaryls and L is an ionizable or leaving group, the compound having at least a pair of enantiomers, wherein one enantiomer of the pair is in an excess of at least 75% ee with respect to the other enantiomer of the pair.

14. The composition as in claim 13 wherein $R^1$ is phenyl and $R^4$ is hydrogen or phenol.

15. The composition as in claim 13 wherein L is a halide, ester, carbonate, or carboxylate.

16. The composition as in claim 13 wherein the compound has one enantiomer in an excess of greater than about 90% ee with respect to the other enantiomer of the pair.

17. The composition as in claim 13 wherein said compound is a diastereomer with each pair of enantiomers having an enantiomer in an excess of greater than 75% ee with respect to the other enantiomer of the pair.

* * * * *